(12) United States Patent
Flury et al.

(10) Patent No.: US 8,785,621 B2
(45) Date of Patent: Jul. 22, 2014

(54) METHOD FOR DISINFECTING SURFACES

(75) Inventors: Meinrad Flury, Kerzers/FR (CH); Rene H. Dietrich, Landschlacht (CH)

(73) Assignee: Joker AG, Kerzers (CH)

( * ) Notice: Subject to any disclaimer, the term of this patent is extended or adjusted under 35 U.S.C. 154(b) by 0 days.

(21) Appl. No.: 13/643,522

(22) PCT Filed: Mar. 16, 2011

(86) PCT No.: PCT/EP2011/053921
§ 371 (c)(1),
(2), (4) Date: Feb. 21, 2013

(87) PCT Pub. No.: WO2011/134715
PCT Pub. Date: Nov. 3, 2011

(65) Prior Publication Data
US 2013/0150313 A1   Jun. 13, 2013

(30) Foreign Application Priority Data

Apr. 26, 2010  (CH) .......................... 600/10

(51) Int. Cl.
*C08B 37/00* (2006.01)
*C07H 5/04* (2006.01)
*C07H 5/06* (2006.01)

(52) U.S. Cl.
USPC .. 536/55.2; 536/18.7; 536/123.1; 536/123.12

(58) Field of Classification Search
None
See application file for complete search history.

(56) References Cited

PUBLICATIONS

Joker AG, "International Search Report," Int'l Patent Application No. PCT/EP2011/053921, filed Mar. 16, 2011 (Jan. 19, 2012).

*Primary Examiner* — Patrick Lewis
(74) *Attorney, Agent, or Firm* — Janet Sleath; Speckman Law Group PLLC

(57) ABSTRACT

A malleable compound according to the invention for use as a disinfectant comprises water, 25 to 40% by weight of a solvent component comprising low-molecular, water-miscible alcohols, 1 to 10% by weight of an active bactericidal component, 3 to 6% by weight hydroxypropylated polygalactomannan with an etherification level of between 0.3 and 1.5 and 0.1 to 0.5% by weight boracic acid or an equivalent amount of boron ions.

10 Claims, No Drawings

METHOD FOR DISINFECTING SURFACES

This application is the US national phase entry of International Patent Application no. PCT/EP2011/053921, filed Mar. 16, 2011, which claims priority to Swiss patent application no. 00600/110 filed 26 Apr. 2010.

TECHNICAL FIELD

The invention relates to a means of disinfecting hard-to-clean surfaces.

STATE OF THE ART

Bacterial infections are currently a major problem in hospitals too, leading to a large number of complications. Although antibiotics have been available for the treatment of bacterial infections for some time now, germs have developed resistance to various antibiotics, particularly in the hospital environment. These sorts of multi-resistant bacteria represent an ever-increasing problem, especially in intensive care medicine, as hospital patients in particular often have a weakened immune system and are therefore particularly susceptible to infection. Very common antibiotic-resistant strains are methicillin-resistant *Staphylococcus aureus* (MRSA) strains, which already account for over 50% of the incidence of disease each year on intensive care wards in the USA.

Similar problems also exist in veterinary practices, because cats and dogs are also frequently MRSA carriers. Studies have shown that here too the improper use of antibiotics leads to multi-resistant germs in domestic pets (*"Occurrence of highly fluoroquinolone-resistant and methicillin-resistant Stapylococcus aureus in domestic animals"*, A. E. Lin, J. E. Davies, Can. J. Microbiol. 53, 925 (2007)). These are then transferred to owners and staff at the veterinary practices, from where they can then be transmitted again to animals and humans (*"High risk for nasal carriage of methicillin-resistant Staphylococcus aureus among Danish veterinary practitioners"*, A. Moodley et al, Scand. J. Work, Envir. & Health 34, 151 (2008)).

The most efficient means of avoiding complications through infection is generally accepted to be avoiding the infection itself through suitable hygiene measures, particularly through regular and adequate disinfection of objects and surfaces with which a patient may come into contact either directly or indirectly. Flat, smooth surfaces can be disinfected relatively easily using traditional liquid disinfectants. Consumables in the hospital sector are usually supplied in presterilised packaging. Instruments and objects that can be used over and over again, such as surgical or medical instruments, on the other hand, can be sterilised in autoclaves.

Everyday objects such as ballpoint pens, mobile phones, pagers, spectacles, computer keyboards, etc., the use of which is unavoidable in hospitals too, are problematic however. Such objects frequently come into contact with hands, which naturally carry a particularly large number of germs. In this way, germs can be spread over a wide area not just by visitors and patients, but particularly by nursing staff too. Another problem is electronic equipment, which can have gaps that are difficult to get into, as in the case of control buttons, for instance. These cannot be reached by traditional surface disinfection and are therefore a haven for germs.

The aforementioned objects cannot usually be placed in an autoclave and liquid disinfectants are not practical, as they cannot penetrate all cracks during surface use. Liquid disinfectants may also damage electronic components. It would therefore be desirable to have a possible way of disinfecting such problematic objects and surfaces simply and effectively too.

WO 02/0557642 discloses a cleaning agent for removing solid particles from surfaces in which a pseudo-plastic polygalactomannan gel compound penetrates narrow gaps and gathers solid particles present there. The gathered particles are incorporated in the compound, so that an unused surface is continuously available for cleaning. The aforementioned cleaning compound is aimed at efficiently gathering dust and fluff. Its surface wetting is insufficient for use as a disinfectant.

OBJECT OF THE INVENTION

The object of the invention is to provide a means of disinfecting surfaces that does not exhibit the aforementioned and other disadvantages. In particular, a disinfectant of this sort should be capable of penetrating even hard-to-reach cracks and killing off any germs living there.

This sort of disinfectant should kill off germs quickly and effectively, thereby satisfying the hygiene requirements in the hospital sector and efficiently preventing germs from spreading. In particular, it should meet the relevant standards, particularly European Standards EN 1040 and EN 13697.

These and other objects are solved by a malleable compound according to the invention for use as a disinfectant wherein the compound comprises: water; 25-40% by weight, preferably 30-35% by weight, of a solvent component comprising low-molecular, water-miscible alcohols; 1-10% by weight, preferably 2-7% by weight, of an active bactericidal component, 3-6% by weight hydroxypropylated polygalactomannan with an etherification level of 0.3-1.5; and 0.1-0.5% by weight boracic acid or an equivalent amount of boron ions. Other advantageous embodiments are described herein.

DESCRIPTION OF THE INVENTION

A malleable compound for use as a disinfectant comprises 25 to 40% by weight, preferably 30 to 35% by weight, of a solvent component comprising low-molecular, water-miscible alcohols, 1 to 10% by weight, preferably 2 to 7% by weight, of an active bactericidal ingredient, 3 to 6% by weight hydroxypropylated polygalactomannan with an etherification level of between 0.3 and 1.5 and 0.1 to 0.8% by weight boracic acid or an equivalent amount of boron ions. The remaining proportions by weight are preferably supplemented with water.

A compound according to the invention is advantageously suitable for gathering small particles, particularly biogenic impurities, on its surface by adhesion. The advantage of this is that apart from the immediate localised disinfectant effect of a compound according to the invention, small particles such as germs, for example, remain adhered to its surface where they are killed off. The exposure time in this case is significantly higher than on the surface being cleaned, which means that the bactericidal effect is absolute. By kneading and moulding the compound, as is automatically the case when the inventive compound is being used in the normal way, the particles are permanently captured within the compound and the replacement surface is able to gather up further foreign particles of a biogenic and non-biogenic nature.

In an advantageous embodiment of this sort of inventive compound, the solvent component is selected from a group comprising ethanol, 2-propanol, methanol, 1-propanol and mixtures thereof. In an even more advantageous variant, the solvent component is ethanol, 2-propanol or a mixture thereof.

Benzalkonium chloride, benzalkonium saccharinate, didecyl dimethyl ammonium chloride, chlorhexidine or a mixture thereof is used as the active bactericidal component of a compound according to the invention.

In another advantageous variant of a compound according to the invention, the etherification level of the hydroxypropylated polygalactomannan is between 0.5 and 1.5. Particularly advantageous is an etherification level between 0.6 and 1.2.

The action of a malleable disinfectant according to the invention is based on this being in the form of a gel compound with pseudo-plastic flow properties, rather than a liquid disinfectant. If a disinfectant according to the invention is pressed onto an everyday object, such as a mobile phone or a computer keyboard, the compound will penetrate the cracks and gaps too. This means that surfaces that would not otherwise be accessible come into contact with the disinfectant too, so that germs are killed off. After the required exposure time, a minute for example, the gel compound is completely removed from the object.

An advantageous compound according to the invention comprises 25 to 40% by weight, preferably 30 to 35% by weight, ethanol or isopropanol or a mixture thereof. Apart from the disinfecting effect, a high ethanol/isopropanol content is particularly beneficial, in order to ensure adequate surface wetting of the surfaces being disinfected, so that the desired disinfectant action is achieved, even with a short exposure time. Further suitable alcohol components are other low-molecular, water-miscible alcohols, such as methanol or 1-propanol, for instance.

To create the basic gel compound of the malleable disinfectant, the latter comprises modified, boron-wetted polygalactomannans. Polygalactomannan, a polysaccharide, is used as a hydrocolloid as a thickening and gelation agent, for example in food technology. Unmodified poly-galactomannans are not soluble in ethanol.

It has been found that in the case of gel cleaning agents, as are known in the state of the art, an increase in the solvent content, as is necessary for a disinfectant according to the invention, results in the gel having an unsatisfactory consistency. Depending on the boron content and pH value, the resulting consistency may be soft and sticky or brittle and crumbly. A gel of this sort no longer has the required pseudo-plastic flow capability, which is necessary to quickly get behind fine cracks and gaps and disinfect the surfaces there.

It was then found that the use of sufficiently hydroxypropylated polygalactomannan improves the gel's tolerance for higher alcohol contents. For this purpose, the etherification level of the polygalactomannan (number of hydroxypropyl groups per anhydrohexose unit of the polygalactomannan) is at least 0.3, preferably 0.5 to 1.5, and particularly preferably 0.6 to 1.2. Tests have shown that an excessively high etherification level leads in turn to an unwanted drop in the elasticity of the gel compound.

A malleable compound according to the invention for use as a disinfectant in accordance with one of the preferred embodiments comprises 3-6% by weight polygalactomannan and also 0.1-0.8% by weight boracic acid with a pH value of between 6 and 10. Boron components suitable for wetting include, for example, sodium tetraborate or boracic acid. The pH value may be adjusted if necessary by adding phosphates, for example trisodium phosphate, or sodium carbonate. On the one hand, the degree of wetting must be set at such a level that the alcohol evaporation rate is not too high, so as to guarantee the storability of the disinfectant and, on the other, so low that adequate surface wetting does not take place.

The viscosity of this sort of compound according to the invention measured at 25° C., is 50,000 to 250,000 mPa·s, preferably between 100,000 and 200,000 and particularly preferably between 120,000 and 180,000 mPa·s.

Substances that are soluble in water and low-molecular alcohols, are effective over a wide pH range, are hydrolysis-stable and advantageously compatible with surfactants are suitable in principle as primary bactericidal and fungicidal active components of a malleable disinfectant according to the invention. The corresponding substance should be essentially harmless to humans and animals. It should not attack the surfaces being cleaned, particularly plastics and other polymer materials. The substance is preferably biodegradable. Suitable active disinfectant components are, for example, quaternary ammonium compounds, such as benzalkonium chloride (alkyl dimethyl benzyl ammonium chloride CAS 68391-01-5), for example, particularly where C12=55%, C14=25%, C16=11%, C18=9%, benzalkonium saccharinate, didecyl dimethyl ammonium chloride (CAS 7173-51-5) or similar. Likewise suitable is chlorhexidine, for example as chlorhexidine gluconate. Aldehydes with disinfectant action, such as formaldehyde and 1,5-pentanedial are likewise effective but can only be used for special areas of application where a sporicide effect is required, on account of their toxicity. The proportion of active disinfectant components is between 1 and 10% by weight, preferably between 2 and 7% by weight.

A compound according to the invention may additionally contain water-soluble, hydrolysis-stable surfactants to further improve surface wetting, for example, non-ionic surfactants, such as polydimethylsiloxane-polyoxyalkylene copolymers, for example.

The remaining proportions by weight of a disinfectant according to the invention, apart from the constituents described, are preferably supplemented with water.

A disinfectant according to the invention was tested for its bactericidal effect, particularly on MRSA (ATTC 43300) using standard tests, in accordance with standard EN 1040 ("Chemical disinfectants and antiseptics—Basic bactericidal activity test method and requirements (phase 1), 1997") and EN 13697 ("Chemical disinfectants and antiseptics—Quantitative non-porous surface test for the evaluation of bactericidal and/or fungicidal activity of chemical disinfectants used in food, industrial, domestic and institutional areas—test method and requirements without mechanical action (phase 2/step 2)").

The tests produced the required reduction in the number of (MRSA) germs by more than 100,000 for both the 1 minute and 5 minute exposure times, which satisfies the requirements of the aforementioned standards.

The invention claimed is:
1. A malleable composition for use as a disinfectant comprising:
  (a) water;
  (b) 25-40% by weight of a solvent component comprising low-molecular, water-miscible alcohols;
  (c) 1-10% by weight of an active bactericidal component;
  (d) 3-6% by weight hydroxypropylated polygalactomannan with an etherification level of 0.3-1.5; and
  (e) 0.1-0.5% by weight boracic acid or an equivalent amount of boron ions.
2. The composition according to claim 1, wherein the composition is suitable for gathering small particles on its surface by adhesion.

3. The composition according to claim 1, wherein the solvent component is selected from the group consisting of: ethanol, 2-propanol, methanol, 1-propanol and mixtures thereof.

4. The composition according to claim 1, wherein the active bactericidal component is selected from the group consisting of: benzalkonium chloride, benzalkonium saccharinate, didecyl dimethyl ammonium chloride, chlorhexidine and mixtures thereof.

5. The composition according to claim 1, wherein the etherification level of the hydroxypropylated polygalactomannan is 0.3-1.5.

6. The composition according to claim 1, wherein the solvent component is present in an amount of 30-35% by weight.

7. The composition according to claim 1, wherein the active bactericidal component is present in an amount of 2-7% by weight.

8. The composition according to claim 2, wherein the small particles are biogenic impurities.

9. The composition according to claim 3, wherein the solvent component is selected from the group consisting of: ethanol, 2-propanol and mixtures thereof.

10. The composition according to claim 5, wherein the etherification level of the hydroxypropylated polygalactomannan is 0.6-1.2.

* * * * *